(12) United States Patent
Bates et al.

(10) Patent No.: US 9,113,700 B2
(45) Date of Patent: Aug. 25, 2015

(54) TOOTHBRUSH TRACKING SYSTEM

(75) Inventors: Susan Bates, Wirral (GB); Derek Guy Savill, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 590 days.

(21) Appl. No.: 13/515,005

(22) PCT Filed: Nov. 25, 2010

(86) PCT No.: PCT/EP2010/068226
§ 371 (c)(1),
(2), (4) Date: Aug. 9, 2012

(87) PCT Pub. No.: WO2011/073010
PCT Pub. Date: Jun. 23, 2011

(65) Prior Publication Data
US 2012/0310593 A1 Dec. 6, 2012

(30) Foreign Application Priority Data

Dec. 17, 2009 (EP) .................................... 09179736

(51) Int. Cl.
*A46B 15/00* (2006.01)
*G06F 15/00* (2006.01)
*A61C 17/00* (2006.01)
(52) U.S. Cl.
CPC ......... *A46B 15/0002* (2013.01); *A46B 15/0006* (2013.01); *A46B 15/0012* (2013.01); *A46B 2200/1066* (2013.01); *A61C 17/00* (2013.01)

(58) Field of Classification Search
CPC .......... A46B 15/0002; A46B 15/0006; A46B 15/0012; A46B 2200/1066
USPC ................................. 433/25, 44, 72; 702/150
See application file for complete search history.

(56) References Cited

U.S. PATENT DOCUMENTS

| 6,485,300 B1 * | 11/2002 | Muller et al. .................... 433/29 |
| 6,536,068 B1 * | 3/2003 | Yang et al. ...................... 15/105 |
| 6,731,213 B1 | 5/2004 | Smith |
| 2006/0141421 A1 * | 6/2006 | Braunecker et al. .......... 433/215 |

FOREIGN PATENT DOCUMENTS

| DE | 4012413 A1 | 10/1991 |
| EP | 0634151 A2 | 1/1995 |
| WO | WO0147392 A1 | 7/2001 |
| WO | WO02083257 A2 | 10/2002 |

OTHER PUBLICATIONS

International Search Report, PCT/EP2010/068226, mailed Apr. 4, 2011, 4 pp.

* cited by examiner

*Primary Examiner* — Andrew Schechter
*Assistant Examiner* — Peter Ngo
(74) *Attorney, Agent, or Firm* — Greenberg Traurig, LLP

(57) ABSTRACT

A method of monitoring tooth brushing comprising: receiving a position signal from a position sensor (601) disposed on a toothbrush (21) comprising a handle and a head (22); receiving a force signal from a force sensor (602) disposed on the toothbrush (21); and calculating a position of the head of the toothbrush using the position signal in combination with the force signal.

13 Claims, 5 Drawing Sheets

TOOTHBRUSH TRACKING SYSTEM

The invention relates to a method and system for tracking a position of a toothbrush head during brushing.

It is well known that many dental problems experienced by individuals who regularly use a toothbrush are associated with poor toothbrush usage. For example, even if brushing occurs several times each day, incorrect brushing habits can result in the brush failing to come into contact with certain areas of the teeth. Poor brushing coverage may also be caused, or at least exacerbated, by the design of the toothbrush.

Current methods of determining the location of plaque in the mouth are generally difficult to use. Two basic methods exist, one of which uses an assessor to visually inspect and then manually record the amount and position of plaque on the teeth. Another method involves the use of a camera to record images of a user's teeth, which can be subsequently analysed. For both methods the plaque needs to be stained in some way to increase its visibility. Both methods have significant drawbacks. For visual inspection, assessors can vary significantly in their assessments, and two people are generally required (one to assess, one to record). For camera recording, the lighting conditions need to be strictly controlled, particularly for a comparison between the appearance of teeth before and after treatments. Recording anything other than the buccal surface is difficult.

Systems have been developed that attempt to address such problems by monitoring the position of a toothbrush during brushing. An example of such a system is disclosed in WO 02/083257, in which the position of a toothbrush is monitored relative to the position of the teeth of an individual, the toothbrush comprising a first position sensor, the output of which is fed to a processing apparatus which also receives an output from a second position sensor mounted in fixed relationship to the teeth. The processing apparatus compares the two sensor outputs to monitor the position of the toothbrush relative to the teeth during brushing.

Other systems have also been developed to monitor the motion of a toothbrush in use in conjunction with a measurement of force applied by the toothbrush head on the teeth of the individual. An example of such a system is disclosed in WO 01/47392, in which a toothbrush includes a motion sensor for determining a brushing motion and a strain gauge or other type of force sensor for determining a force applied during brushing. This system is not, however, configured to determine the relative position between the toothbrush head and the teeth of the user. Force measurements are used to indicate the pressure applied during brushing. U.S. Pat. No. 6,731,213 also discloses a tooth brushing monitoring system in which force information is obtained from a toothbrush that may also incorporate a position sensing device capable of detecting position of the toothbrush within a user's mouth.

When determining the position of the toothbrush head relative to the teeth in a system such as in WO 02/083257, tracking inaccuracies can occur. During brushing the toothbrush handle can flex, which changes the relative position of the position sensor (typically mounted on the handle of the toothbrush) to the toothbrush head. There also exist other inherent positional errors in tracking systems based on position sensing and on motion sensing. These tracking difficulties make fitting positional data from toothbrush tracking to a model of the user's teeth problematic, since it may not be known to a sufficient degree of accuracy where the toothbrush head is in relation to the teeth at any moment during brushing.

It is consequently an object of the invention to address one or more of the above mentioned problems.

In accordance with a first aspect of the invention there is provided a method of monitoring tooth brushing comprising:
   receiving a position signal from a position sensor disposed on a toothbrush comprising a handle and a head;
   receiving a force signal from a force sensor disposed on the toothbrush; and
   calculating a position of the head of the toothbrush using the position signal in combination with the force signal.

The invention addresses the inherent tracking problem in existing systems that result from flexing of the toothbrush head relative to the toothbrush body on which the position sensor is provided by using the force signal in addition to the position signal to calculate a position of the toothbrush head.

The position of the toothbrush head may be determined by augmenting a position of the head indicated by the position signal with a calculation of a deflection of the head relative to the handle determined from the force signal. The position signal may be derived from a sensor that is disposed in, or mounted on, the toothbrush at a location offset from the toothbrush head. The augmentation of this offset allows the flexed position of the head to be determined relative to an unflexed state, and therefore a more accurate position of the head to be determined.

The deflection is preferably determined as a function of the force signal and the mechanical properties of the toothbrush, which will have been determined beforehand. The mechanical properties of the toothbrush will preferably comprise a measure of flexural stiffness in one or more directions. In certain embodiments, the flexural stiffness in two directions orthogonal to a longitudinal axis of the toothbrush may be used, together with force signals from two force sensors in the toothbrush, to determine the toothbrush head flexure in directions lateral and normal to the teeth of an individual.

The invention may be used in combination with a model of an individual's teeth to assess a tooth brushing action on an individual tooth basis. Customised upper and lower dentition models may for example be provided in accordance with the disclosure of WO 2008/116743, in which the position and orientation of a toothbrush relative to the teeth whilst tooth brushing is determined using a six degree of freedom sensor attached to the handle of the toothbrush. A similar sensor is also described in WO 02/083257. Alternatively, the invention itself may be used to build up a model of an individual's teeth during brushing.

The lateral and normal forces applied to the teeth by the subject during brushing may be measured using a force or pressure sensor attached to the toothbrush, for example in the head of the toothbrush or in a part of the toothbrush connecting the head to the handle.

The positional and force data may be transmitted to a data analysis unit by wired or wireless means from the toothbrush, the data analysis unit configured to perform the calculations necessary to determine the uncorrected positional data from the position sensor and apply an offset to the uncorrected positional data using the force signal to derive a position of the toothbrush head.

An advantage of the invention is that analysis of the positional and force data provides more accurate information regarding the position of the toothbrush head at any instant in time. A further advantage is that the force signal can be used to also provide a measure of force being experienced by the brush head at that instant, which is useful for analysing brushing behaviour, for example to determine where excessive or too little pressure is being applied.

The accuracy of the positional data can be continuously optimised, either in real time or in post-capture analysis, by correcting for flexure in the toothbrush handle using knowledge of the physical characteristics of the toothbrush handle material when subjected to forces typically applied during tooth brushing. This information may be gathered by prior measurement of toothbrush handle behaviour under controlled force conditions, or can be calculated using computer modelling such as finite element analysis (FEA).

Tooth contact can also be detected using force measurements. This can be used together with the positional data to accurately predict where the tooth surface is, thus improving the accuracy of the system.

The invention is described in further detail below by way of example, with reference to the appended drawings in which.

Figure 1:
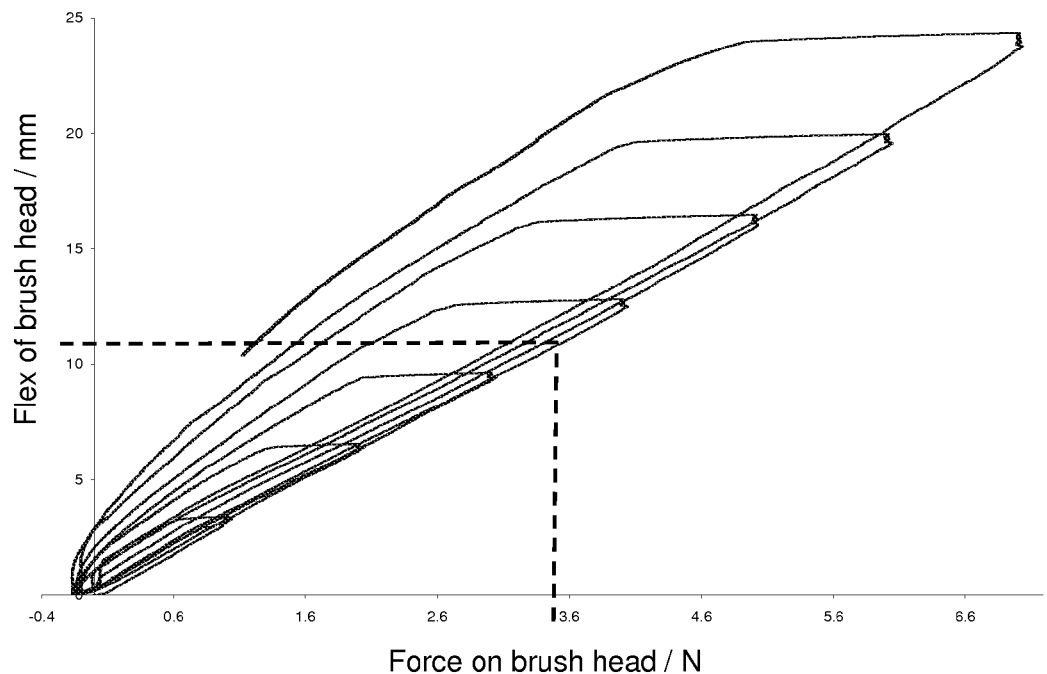
FIG. 1 is a series of measurements indicating the degree of flexure of a toothbrush head as a function of force applied to the brush head.

FIG. 1 illustrates a series of measurements taken on a typical polypropylene toothbrush, in which a force was applied to the toothbrush head and the flexure of the head measured while the toothbrush handle remained fixed. It can be seen that the toothbrush head flexes up to around 25 mm from its unflexed position when a load of around 7 N is applied. A degree of hysteresis is also evident from the measurements, due to the viscoelastic nature of the material used to make the toothbrush. A typical degree of force applied during brushing would be around 3.5 N, which relates to a flexure of at least 11 mm (illustrated in FIG. 1 with dotted lines).

Figure 2A:
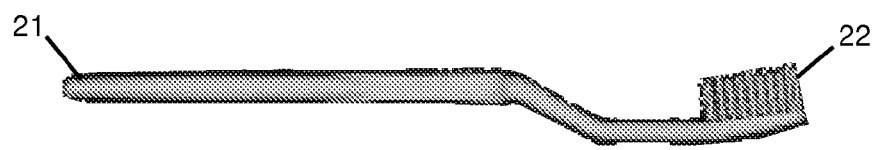
FIG. 2a is a drawing of a toothbrush in an unflexed state.
Figure 2B:
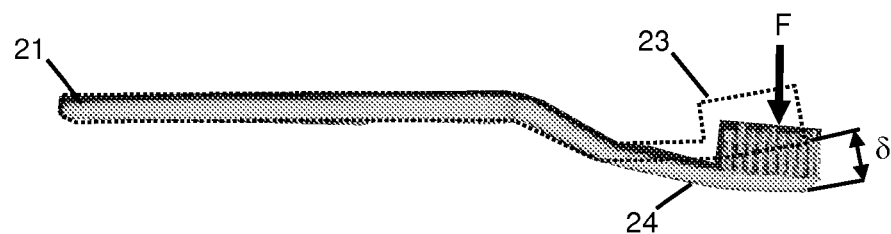
FIG. 2b is a drawing of the toothbrush of FIG. 2a in a flexed state.

FIGS. 2a and 2b illustrate results derived from a computer model of a toothbrush. With no force applied, the toothbrush 21 is in the unflexed state shown in FIG. 2a. With a force F applied to the toothbrush head 22, the unflexed shape of the toothbrush 21 (indicated by dotted line 23 in FIG. 2b) changes to a flexed state 24. A deflection δ of the toothbrush head 22 results. The result shown in FIG. 2b results from a modelled force of around 10 N applied to the toothbrush head 22, resulting in a deflection δ of over 25 mm, as would be expected from the mechanical test results shown in FIG. 1.

In general, therefore, the mechanical properties of the toothbrush comprise at least a measure of flexural stiffness, and optionally a measure of hysteresis, in one or more directions, for example in two directions orthogonal to a longitudinal axis of the toothbrush. The mechanical properties may be determined by physical testing, finite element analysis (FEA) or both.

Using a force sensor in or on the toothbrush allows the deflection of the head relative to the handle to be determined. The force sensor may be configured to measure the normal force on the toothbrush head, for example a sensor of the type disclosed in WO 01/47392, in which a force sensor is disposed in the connecting portion of the toothbrush between the handle and the head. The force sensor may also be configured to measure a force transverse to the normal force.

Figure 3A:
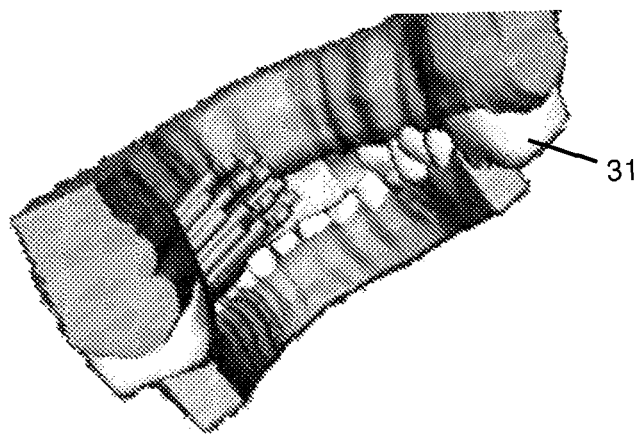
FIGS. 3a and 3b are computer-generated images showing a calculated position of a toothbrush head relative to a set of teeth using positional data alone.
Figure 3B:
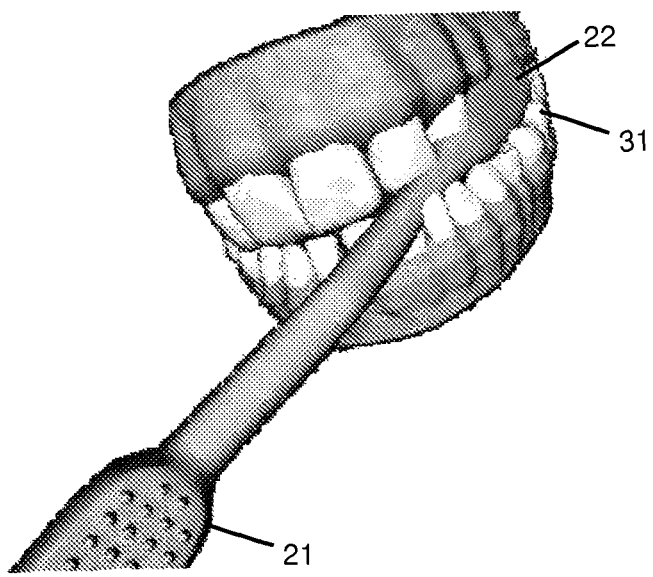

As an illustration of the effect of uncorrected positional data being used, FIGS. 3a and 3b show different views from a rendered computer model of a set of teeth 31 together with a model of a toothbrush 21 in position relative to the teeth 31 according to uncorrected positional data. Due to the toothbrush flexing in use, the head 22 of the toothbrush is shown in a clearly incorrect position, with the head 22 interfering with the teeth 31.

Figure 4:
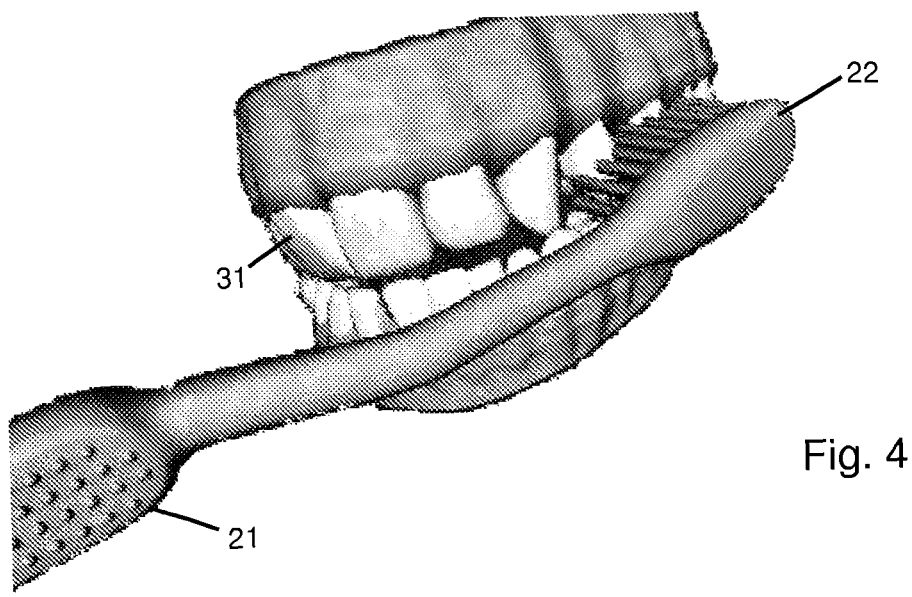
FIG. 4 is a computer-generated image showing the effect of a calculated position of a toothbrush head relative to a set of teeth when a force signal is taken into account.

FIG. 4 illustrates a rendered model of the set of teeth 31 when a correction is applied to the positional data from the toothbrush 21 by using force information from the toothbrush head to apply a deflection to the head position shown in FIGS. 3a and 3b. As can be clearly seen, the toothbrush head 22 no longer interferes with the teeth 31. A more accurate assessment of brushing action in relation to the teeth can therefore be derived.

Figure 5:
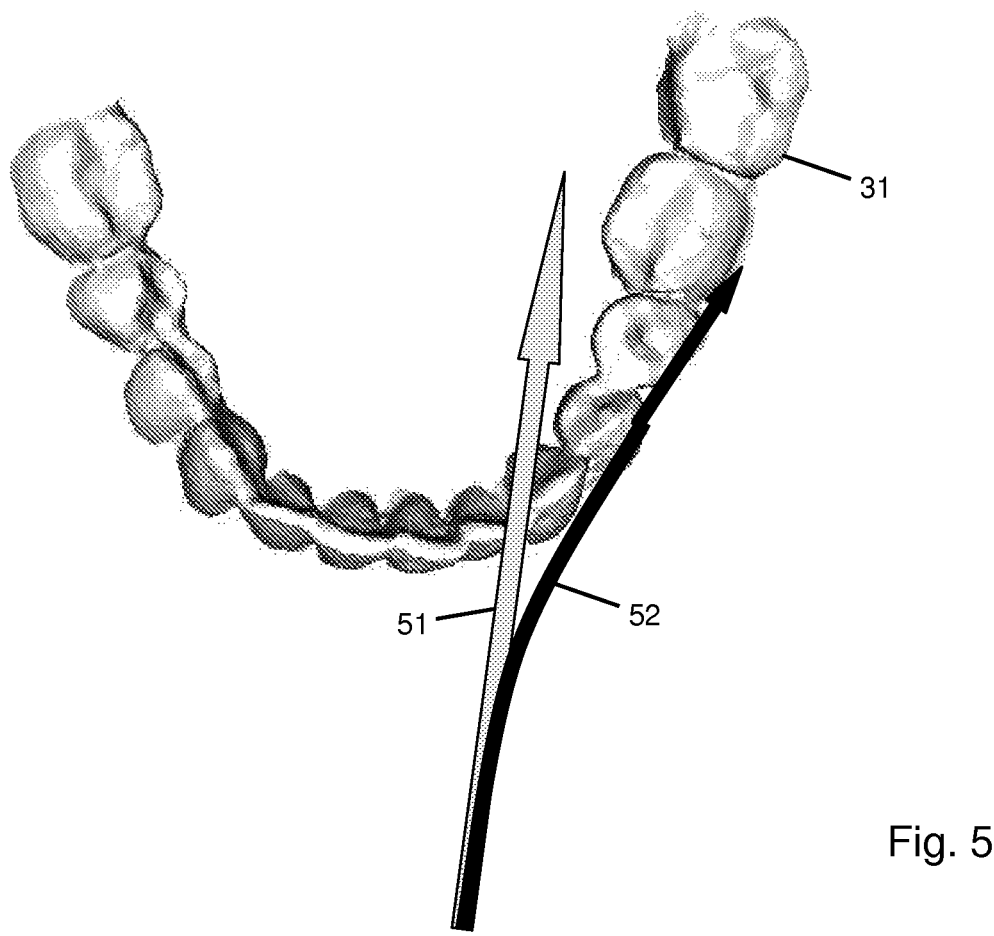
FIG. 5 is a plan view of a set of teeth indicating the effect of taking a force signal into account when determining position of a toothbrush head.

FIG. 5 shows another view of the set of teeth 31, in this case indicating a plan view of the lower set of teeth, with two arrows 51, 52 indicating the uncorrected and corrected position of the toothbrush.

Figure 6:
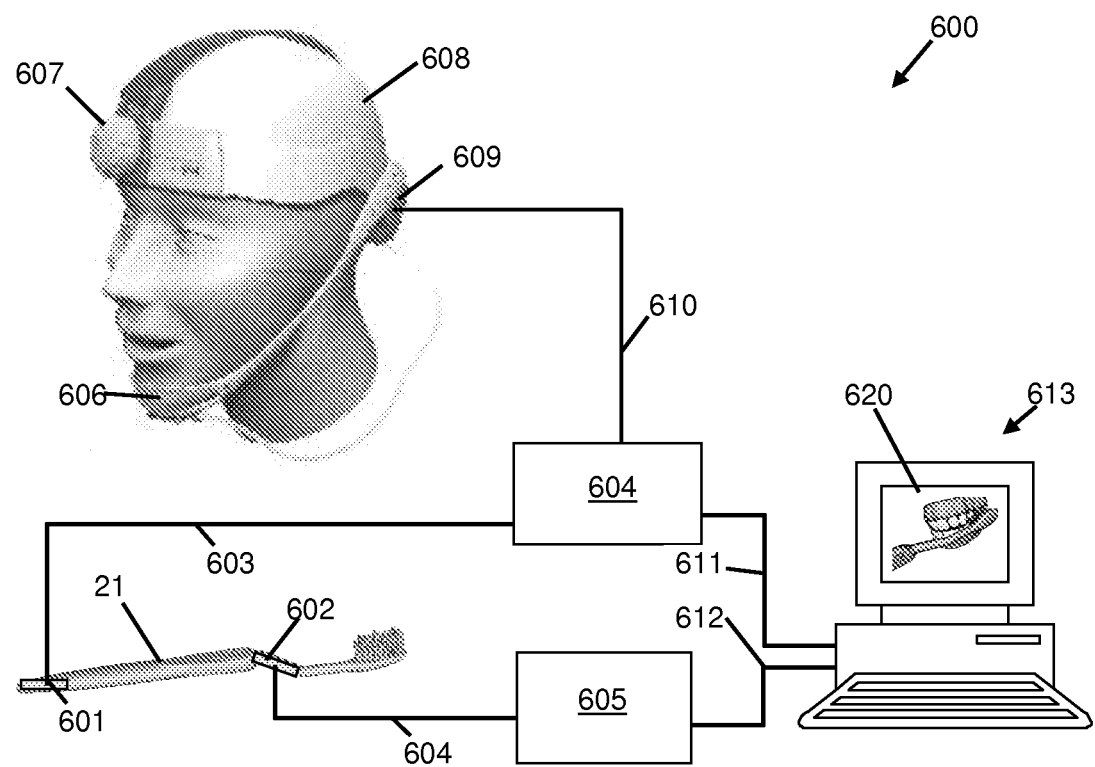
FIG. 6 is a schematic diagram of a system comprising a toothbrush and a data processing unit.

FIG. 6 illustrates a schematic view of a system 600 according to an embodiment of the invention, which is based on the commercially available 'Oral Insights' system, as for example described by J-P. Claessen et al., in "Designing interventions to improve tooth brushing", IDJ (2008) 58, 307-320. Further information relating to this system is also disclosed by G. Savill et al., in "*Toothbrush Tracking System: novel tool for recording motion and position*", abstract 0101, PEF IADR, Baltimore, 2008, by S. Bates et al., in "*Efficacy of Oralinsights OHI System in General Dental Practice*", abstract 0428, PEF IADR, London, 2008 and by A. M. Lloyd et al., in "*Efficacy of Oralinsights OHI System for Targeted Plaque Removal*", abstract 0429, PEF IADR, London, 2008. A toothbrush 21 comprises a position sensor 601 and a force sensor 602, the position sensor 601 being located in the handle of the toothbrush 21 while the force sensor 602 is located between the handle and the toothbrush head. Information from the position sensor 601 is transmitted via a link 603 to a position calculation unit 604, and information from the force sensor 602 is transmitted via link 604 to a force calculation unit 605. The position calculation unit 604 and force calculation unit 605 preferably form part of a common unit, and a common link may be provided from the toothbrush 21 to the common unit for transmission of both position and force signals. The link 604 may be provided by wired or by wireless means (for example via a Bluetooth™ connection).

The position calculation unit 604 also receives signals from a position sensing unit located on the head of the user 608, the position sensing unit comprising a headset incorporating a magnetic field transmitter 607 and a six degrees of freedom sensor 606. The six degrees of freedom sensor 606 is preferably attached to a chin strap. The positional signal from the position sensing unit 606 is transmitted by a transmitter 609 to the position calculation unit 604 via a link 610, which may also be wired or wireless.

The position calculation unit 604 sends data representing the positions of the toothbrush handle position sensing unit 601 and the sensor 606 attached to the user 608 to a computer 613 via a link 611. The force calculation unit 605 sends data representing force applied to the toothbrush head to the computer 613 via a link 612. From this, the computer 613 is able to calculate the corrected position of the toothbrush head, and may also be configured to display, preferably in real time, a computer-generated model of the user's teeth on a monitor screen 620. The display can be used to provide immediate feedback to the user on the effectiveness, or otherwise, of their tooth brushing.

The computer 613 may alternatively derive the information only once a set of data has been received.

The positional and force information may optionally be transmitted wirelessly from the toothbrush 21 to the force and position calculation units 604, 605, for example by means of a Bluetooth or WiFi connection. The positional and force information may optionally be temporarily stored in a memory in the toothbrush and transmitted to the calculation units 604, 605 once brushing is complete, for example when the toothbrush is inserted into a charging cradle.

An optical probe may also be incorporated in the toothbrush head, for example to enable a recording can be made of the location of plaque. Images from the optical probe can be recorded from the oral cavity together with the corrected position data. Combining the data enables the position of the plaque relative to the teeth to be accurately determined. The system could also be used for the detection of caries.

Because the system can be used to determine an accurate position of the toothbrush head, the system may also be used to collect data for reconstructing an image of a user's jaw. Corrected positional data from the toothbrush 21 may be used in conjunction with image data from an optical probe in the toothbrush head to construct an image map of the user's teeth.

Other sensors such as fluoride, pH, sulphur, zinc or whitening sensors may be incorporated into the toothbrush. The system may also be used for mapping of tooth condition, for example in determining wear, erosion, demineralisation, white spot and so on.

Figure 7:
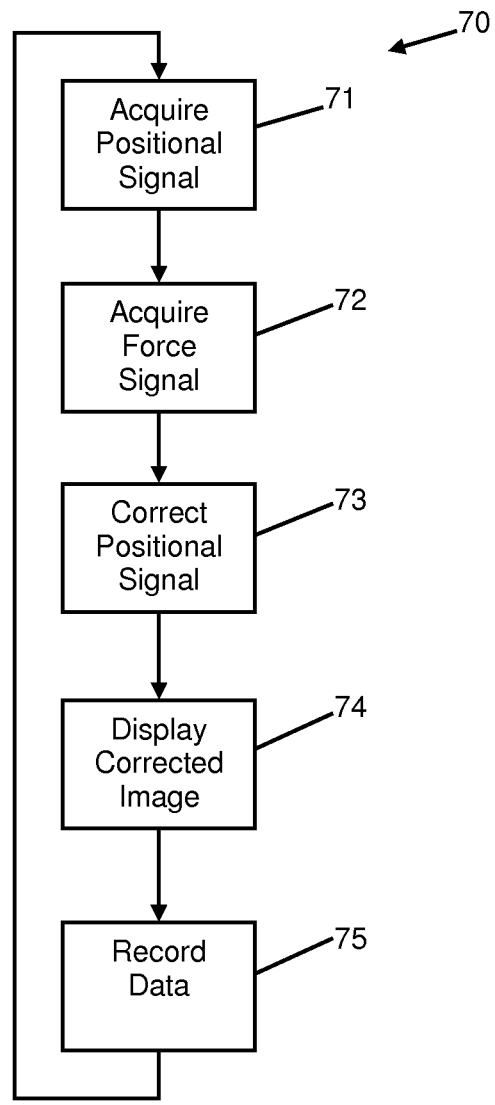
FIG. 7 is a flow diagram of an event cycle for the system illustrated in FIG. 6.

FIG. 7 illustrates a flow diagram of an event cycle 70 for the system 600 illustrated in FIG. 6. As a first step 71, a positional signal is acquired from the position sensor 601 in the toothbrush 21 and the position sensor 606 on the user's headset. In a second step 72, which may be simultaneous with or immediately preceding the first step, a force signal is acquired from the force sensor 602 on the toothbrush 21. In a third step 73, once the position and force signals are acquired, the position signal from the toothbrush 21 is corrected using the force signal from the force sensor 602. In a fourth step 74, the display 620 is updated with the corrected position signal, and in a fifth step 75, which may alternatively be simultaneous with or immediately preceding the fourth step 74, the corrected positional data is recorded for later analysis. The event cycle 70 then repeats, going back to the first step 71.

In an exemplary embodiment, the position and force sensors are polled at regular intervals and calculations made during each interval of the position and orientation of the toothbrush relative to the teeth. An appropriate toothbrush model may be applied to determine the position of the head relative to the position sensor and how the head flexes relative to the handle for a range of applied forces. A library of such models may be provided for this purpose, the individual models in the library being the result of physical testing and/or modelling of particular brushes. The library of models may be created by applying known forces to the brush head under stringent physical conditions, and capturing images of the toothbrush before and after force is applied. The images can then be converted into 3D models which are installed and utilised in the system.

The toothbrush model for the brush being used is applied each time the position and orientation of the head is calculated. The system can also be configured to analyse for collision (or interference) between the brush head bristles and the user's teeth and, if so, which tooth faces were affected. Collision detection may be achieved by determining an intersection between a bounding box of the tooth model and a bounding box representing the area of the bristled area of the brush head. For collision between the brush head bristles and a tooth, the system works out which face was hit, for example by considering the angle of a vector along the centre bristle of the brush head, i.e. the angle of the brush head relative to each surface of a tooth, to determine which surface or surfaces are being brushed at that moment.

Provided the calculations can be carried out sufficiently quickly, the position/orientation data is captured essentially in "real time", allowing the corrected position of the toothbrush relative to the teeth to be viewed in real time by the user during brushing. The information could also be captured and corrected after the brushing event.

Various types of sensing technologies may be used to measure position, for example devices based on magnetic sensing, optical sensing, ultrasound, radio waves, GPS or inertia sensing. A preferred way of measuring force is through use of one or more strain gauges in a wheatstone bridge arrangement, although other types of sensors may be used, such as those based on fibre optics, force sensing resistors, piezoelectrics or through measurement of current drawn from an electric motor driving an electric toothbrush. An example of a force sensor used in tooth brushing is disclosed by P. A. Heasman in "*Toothbrushing forces in children with fixed orthodontic appliances*", British journal of Orthodontics vol. 25, 1998, pp. 187-190.

Other embodiments are also within the scope of the invention, as defined by the appended claims.

The invention claimed is:

1. A method of monitoring tooth brushing comprising:
receiving a position signal from a position sensor disposed on a toothbrush comprising a handle and a head;
receiving a force signal from a force sensor disposed on the toothbrush;
calculating a position of the head of the toothbrush using the position signal in combination with the force signal, wherein the position of the toothbrush head is determined by augmenting a position of the head indicated by the position signal with a calculation of a deflection of the head relative to the handle determined from the force signal.

2. The method of claim 1, wherein the deflection is determined as a function of the force signal and predetermined mechanical properties of the toothbrush.

3. The method of claim 2 wherein the mechanical properties of the toothbrush comprise a measure of flexural stiffness in one or more directions.

4. The method of claim 3 wherein the mechanical properties of the toothbrush comprise measures of flexural stiffness in two directions orthogonal to a longitudinal axis of the toothbrush.

5. The method of claim 4 wherein force signals from two force sensors in the toothbrush are used to determine the toothbrush head flexure in directions lateral and normal to the teeth of an individual.

6. The method of claim 5 wherein the lateral and normal forces applied to the teeth are measured using a force or pressure sensor attached to the toothbrush.

7. The method of claim 1 wherein the positional and force data are transmitted to a data processing unit, the position of the head of the toothbrush calculated by the data processing unit.

8. The method of claim 7 wherein a computer model of the teeth of the user is combined with the position of the head of the toothbrush to determine an indication of brushing effectiveness.

9. A tooth brushing monitoring system comprising:
a toothbrush comprising a handle and a head, the toothbrush comprising a position sensor and a force sensor; and
a data processing unit configured to receive a force signal from the force sensor and a position signal from the position sensor,
wherein the data processing unit is configured to calculate a position of the head of the toothbrush from a combination of the position signal with the force signal by augmenting a position of the head indicated by the position signal with a calculation of a deflection of the head relative to the handle determined from the force signal.

10. The tooth brushing monitoring system of claim 9 wherein the data processing unit is remote from the toothbrush.

11. The tooth brushing monitoring system of claim 10 wherein the data processing unit is configured to wirelessly receive the position and force signals from the toothbrush.

12. The tooth brushing monitoring system of claim 9 wherein the toothbrush head comprises an optical probe.

13. The tooth brushing monitoring system of claim 9 wherein the toothbrush head comprises a chemical sensor.

* * * * *